Figure 1:
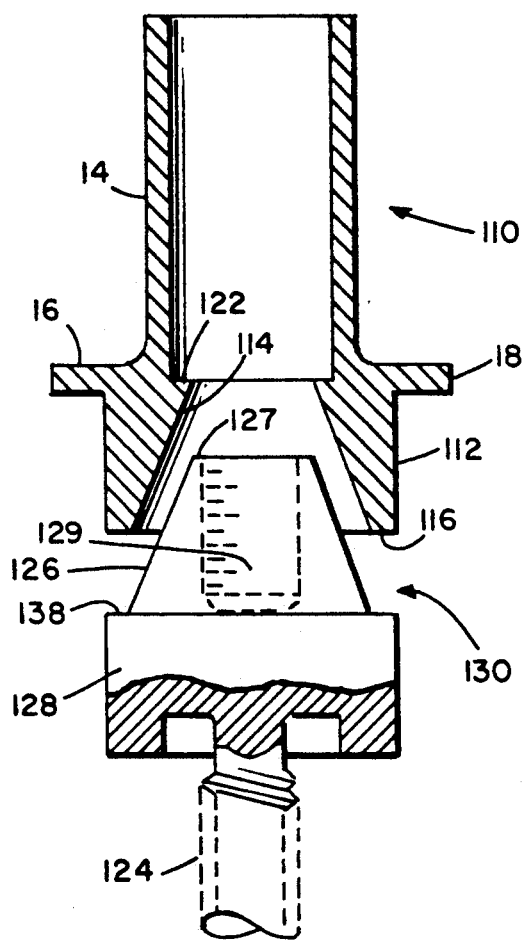

United States Patent [19]

Lazzara et al.

[11] Patent Number: 5,006,069
[45] Date of Patent: Apr. 9, 1991

[54] PERIODONTAL RESTORATION COMPONENTS

[75] Inventors: Richard J. Lazzara, Lake Worth; Keith D. Beaty, West Palm Beach, both of Fla.

[73] Assignee: Implant Innovations, Inc., West Palm Beach, Fla.

[21] Appl. No.: 266,073

[22] Filed: Nov. 2, 1988

[51] Int. Cl.$^5$ .............................................. A61C 8/00
[52] U.S. Cl. ..................................... 433/173; 433/174
[58] Field of Search ............... 433/173, 174, 175, 176, 433/201.1, 220, 221

[56] References Cited

FOREIGN PATENT DOCUMENTS 288445 10/1988 European Pat. Off. ............ 433/173
3726616 9/1988 Fed. Rep. of Germany ...... 433/174
455370 7/1988 Sweden .

Primary Examiner—Cary E. Stone
Attorney, Agent, or Firm—Alfred H. Rosen

[57] ABSTRACT

A dental coping in the form of an elongated tubular body has a base portion adapted at a first end of the body to mate with the gingival aspect of the patient's implant fixture, and a thin-walled tubular portion extending to the other end of the body supragingivally from the base portion when the base portion is so mated. The base portion is substantially rigid, having a thicker sidewall than the thin-walled tubular portion. A shoulder is provided within the base portion for cooperating with a bolt to fasten the coping to the implant fixture. A flange extends outwardly fropm the coping, preferably from the rigid base portion, for fixing in place a temporary restoration formed around the coping. A conical socket in the base portion mates with a conical post on the implant fixture. The fabrication and use of fixed provisional restorations in partially edentulous patients undergoing treatment with osseointegrated fixtures is described.

11 Claims, 1 Drawing Sheet

PERIODONTAL RESTORATION COMPONENTS

This invention relates in general to restorative dentistry, and more particularly to methods and means for fixing a temporary dental restoration to an underlying support such as a dental implant fixture or the like. The invention provides for the fabrication and use of fixed provisional restorations in partially edentulous patients undergoing treatment with osseointegrated fixtures.

While the field of restorative dentistry has made significant advances in the use of dental implants to support dental restorations intended to replace natural teeth, and intended for long-lasting use, very little attention, if any, has been given to providing a temporary restoration supported on a patient's implant fixture (or fixtures) for use while the permanent restoration is being prepared. Yet, dental restoration cases can take as long as one year, sometimes longer, to complete, from the time when the patient is prophylactically prepared to begin the series of treatments required in the fabrication of permanent dental restorations. During that rather extended time interval a patient has need for inexpensive and reliable temporary dental restoration. Dental materials for use in chair-side preparation of temporary restorations are available for other, earlier, forms of restoration, on the patient's own prepared tooth-roots, for example, but up to now the field of restorative dentistry has lacked the ability to provide a temporary dental restoration supported on a dental implant fixture.

A widely-used form of dental implant fixture consists essentially of a generally cylindrical body implanted in a cylindrical bore made in the patient's jawbone, and having an internally-threaded cylindrical socket in which to fasten components used for attaching a permanent restoration to the implant fixture. The invention is illustrated and described with reference to implant fixtures taking that form. Generally according to the invention a dental coping in the form of an elongated tubular body has a base portion adapted at a first end of the body to mate with the gingival aspect of the patient's implant fixture, and a thin-walled tubular portion extending to the other end of the body supragingivally from the base portion when the base portion is so mated. The base portion is substantially rigid, having a thicker sidewall than the thin-walled tubular portion. A shoulder is provided within the base portion, for cooperating with a bolt to fasten the coping to the implant fixture. A flange extends radially outward from the coping, preferably from the rigid base portion, for fixing in place on the coping a temporary restoration formed around the coping. Such a restoration may be formed of the acrylic material that is currently in wide-spread use by prosthodontists for making temporary crowns and bridges.

More particularly, the present invention provides a dental coping for used with a support which includes a supragingivally-extending male cone element for mating with the base portion of the coping. The interior diameter of the base portion is reduced progressively from the first end of the tubular body to the shoulder on the locus of a female cone that is coaxial with the tubular body, providing a conical socket in the base portion having its wider opening at the first end and its narrower opening at the shoulder. This socket is dimensioned to mate with the male cone of the support. The diameter of the wider opening of the socket is smaller than the exterior diameter of the base portion at the first end, providing an annular contact surface at the first end. The support has an annular surface on a shoulder around the base of the male cone providing an annular bearing surface for receiving the annular contact surface of the first end of the base portion of the coping. The axial height of the male cone measured from the bearing surface is preferably less than the axial length of the socket measured between the contact surface and the shoulder.

Copings according to the invention may be made of a variety of materials which resist corrosion in the human mouth over a short term of one year, more or less. Among metals, palladium-silver alloy, stainless steel and aluminum are suitable materials. Among plastics materials, acrylics, similar to crown and bridge materials, may be used. Other choices may be made. Another consideration is to choose a material having adequate resistance to deformation on loading, for the prosthesis being contemplated. In use, a temporary crown is fashioned around the coping, and the thin-walled tubular portion is cut to a suitable length for the crown. The bolt used to fasten the crown to the implant fixture is manipulated through the hole in the coping, and the hole is then filled with a temporary plug, to be drilled out later when access to the bolt is required to remove the temporary crown from the implant fixture. Such access may be required several times, to try-in a partially-prepared permanent restoration and, finally, to install the permanent restoration. Copings according to the invention are sufficiently rugged to permit such repeated installation and removal, while at the same time being inexpensive, and disposable, without damage to the underlying implant fixture, or to the temporary crowns carried on them.

Figure 2:
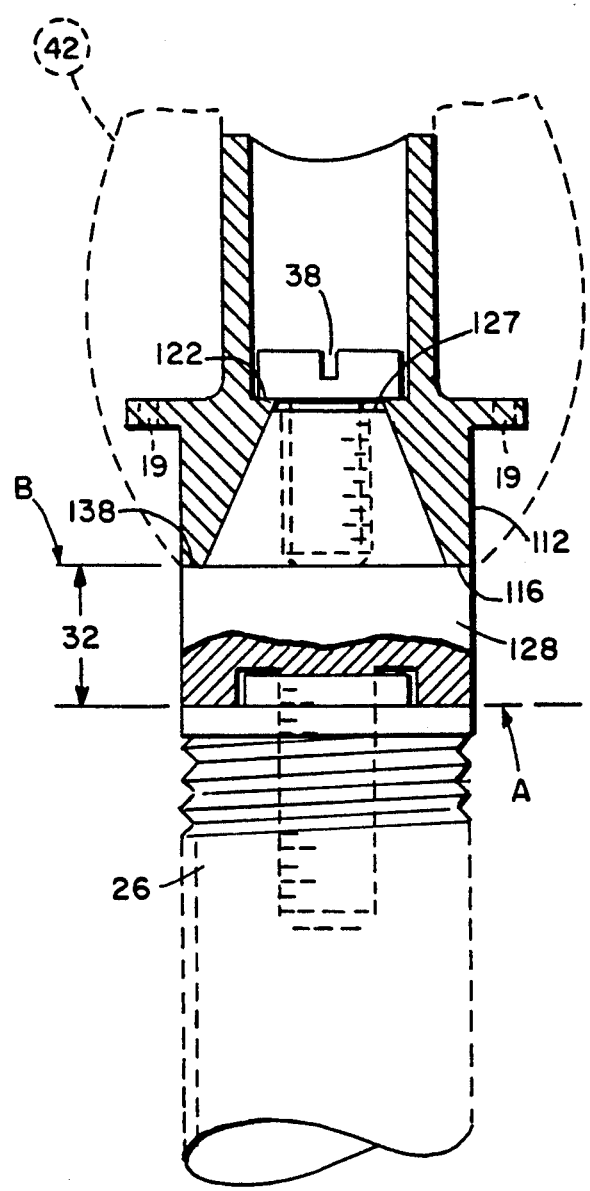

Other advantages and features of the invention will be apparent from the description of an exemplary embodiment of it which follows, with reference to the accompanying drawings, in which:

FIG. 1 shows in longitudinal section a coping according to the invention for use with a tapered-post component; and FIG. 2 illustrates the coping of FIG. 1 joined to an implant fixture via the tapered-post component shown in FIG. 1.

In the drawings a dental coping 110, generally tubular in shape, has a base portion 112 and a relatively thin-walled portion 14 joined end-to-end. An annular retaining flange 16 extends radially outward from the coping in the region where the two portions join each other. This flange 16 may terminate in a peripheral boundary 18 which has a non-circular configuration (not shown). The exterior diameter of the base portion 112 is larger than the exterior diameter of the thin-walled portion 14. The base portion 112 of the coping 110 is internally tapered on the locus of a female cone 114 the diameter of which tapers inwardly with increasing axial distance from a larger diameter at the lower end 116 to a smaller diameter where it terminates at a shoulder 122. The female cone 114 is coaxial with the dental coping 110. The larger diameter of the cone 114 at the lower end 116 is smaller than the exterior diameter of the base portion 112, providing an annular contact surface at the lower end 116.

The dental coping 110 is intended for use with a dental implant fixture of known design, exemplified by the fixture 26 shown in FIG. 2. In use, such a fixture is implanted in a patient's jawbone (not shown) the gingival surface of which is indicated by a dashed line A in FIG. 2. The outer surface of overlying gum tissue 32 is represented by another dashed line B. An integrated tapered-post component 130 has a transmucosal section 128, a supragingivally-extending male post section 126 the diameter of which tapers on the locus of a cone from a larger diameter at the transmucosal section 128 to a smaller diameter at the supragingival end 127, and a screw bolt 124 extending in the opposite direction from the transmucosal section 128 for fixing the integrated post component 130 on the implant fixture 26. An internally-threaded bore-socket 129, coaxial with the screw bolt 124, is provided through the supragingival end 127 into the male post section 126. The female cone 114 of the coping 110 is desirably on the same cone angle as the male post section 126 of the post component 130, providing a socket for the male post section. In the post component 130 the post section 126 meets the transmucosal section 128 at an annular shoulder 138 which has the same dimensions as the annular meeting surface of the lower (gingival) end 116 of the coping 110.

In use the integrated tapered-post component 130 is fixed to the implant fixture 26 with the screw bolt 124 and the socket 114 in the base portion 112 of the coping is fitted over the post section 126. The bolt 38 screws into the bore socket 129 and cooperates with the shoulder 122 to fix the coping 110 to the integral post component 130. The annular surfaces 116 and 138 are maintained in contact with eachother. The combination of female cone-to-male cone contacts 114, 126 provides a stable rigid connection between the coping 110 and the post component 130. To assure firm contacts, and a rigid connection, the male post section 126, measured between the annular contact surface 138 and the supragingival end 127, is axially shorter than the female cone 114, measured between the lower end 116 of the coping 110 and the shoulder 122.

The coping 110 is intended for use in removably fixing a provisional or temporary dental restoration on the support consisting of the dental implant fixture 26 and the post component 130. A temporary dental restoration, outlined by a dashed line 42, is mounted on the coping, embracing the base portion 112 and the retaining flange 16, and extending supragingivally around the thin-walled portion 14. The thin-walled portion can be cut to the length suitable for the crown being fashioned. The bolt 38 is installed through the tubular opening in the tubular portion 14. The latter opening may then be plugged with a temporary dental cement (not shown). The temporary dental restoration 42 may be fashioned of any of the dental materials available for making temporary dental crowns and bridges (e.g.: acrylics). The retaining flange 16 will keep it from moving axially along the coping 10, while the non-circular boundary 18 will restrict the temporary restoration from rotation around the axis of the coping. The peripheral boundary 18 can take shapes other than non-circular; for example, it can be round with saw-tooth serrations. Holes 19 can be provided through the flange 16 (FIG. 2) into which the dental crown or bridge material can penetrate, for additional retention.

In addition to providing for the fabrication and use of fixed provisional restorations in partially endentulous patients undergoing treatment with osseointegrated fixtures, this invention serves as a diagnostic aid and an adjunct in tissue healing, and provides a back-up prosthesis for maintenance and a means for immediate verification by the patient of the benefits of tissue-integrated prosthesis.

We claim:

1. A dental coping for mounting a temporary dental restoration and fixing the same removably on a support such as a dental implant fixture or the like, comprising an elongated tubular body made of a material that resists corrosion in the human mouth around which to mount said restoration, said body having a substantially rigid base portion adapted for mating at a first end of said body with said support, means within said base portion providing a shoulder for cooperation with means to fasten said body to said support, extending supragingivally from said base portion when so fastened a relatively thin-walled tubular portion terminating at the other end of said body, the interior diameter of said base portion being reduced progressively from said first end to said shoulder on the locus of a female cone, providing a conical socket in said base portion having its wider opening at said first end and its narrower opening at said shoulder, and flange means located intermediate said ends of said body and extending radially outward beyond the exterior of said body, said flange means presenting a first substantially flat annular side facing toward but spaced from said first end and a second substantially flat annular side facing toward but spaced from said other end of said boby, said annular sides being substantially co-parallel, said flange means serving to project into and thereby to retain said restoration when the material of the latter is mounted around said body so as to embrace both sides of said flange means.

2. A dental coping according to claim 1 in which said base portion has a larger exterior diameter than said thin-walled portion, and said flange means extends from said base portion near the juncture of said two portions.

3. A dental coping according to claim 1 which the diameter of said wider socket opening is less than the external diameter of said base portion at said first end, providing at said first end an annular contact surface for making contact with said support.

4. A dental coping according to claim 1 in which said exterior flange means extending radially outward from said body terminates in an outer peripheral boundary having means for retaining a restoration, when present around said body and enveloping said flange, against movement around the tubular axis of said body.

5. A dental coping according to claim 4 in which said exterior flange extends radially from said base portion near the juncture of said two portions.

6. A dental coping according to claim 1 in combination with a support which includes a supragingivally-extending male cone element for mating with said socket.

7. A combination to claim 6 in which said support has around the base of said cone element a radially-extending shoulder providing an annular bearing surface.

8. A combination according to claim 7 in which the diameter of said wider socket opening is less than the external diameter of said base portion at said first end of said dental coping, providing at said first end an annular meeting surface for making contact with said bearing surface.

9. A combination according to claim 8 including fastening means engageable between said male cone element and said shoulder in said base portion for holding said socket tightly engaged on said male cone element.

10. A dental coping according to claim 1 in combination with a temporary restoration that envelops said coping including said exterior flange means.

11. A combination according to claim 10 in which said exterior annular flange means extending radially outward from said body has means at its periphery for retaining said restoration against movement around the tubular axis of said body.

* * * * *